(12) United States Patent
Miqbel

(10) Patent No.: US 12,557,840 B2
(45) Date of Patent: Feb. 24, 2026

(54) PORTABLE SCENT DISPENSING ASHTRAY

(71) Applicant: Asad Hasan Miqbel, Lodi, CA (US)

(72) Inventor: Asad Hasan Miqbel, Lodi, CA (US)

( * ) Notice: Subject to any disclaimer, the term of this patent is extended or adjusted under 35 U.S.C. 154(b) by 525 days.

(21) Appl. No.: 17/225,087

(22) Filed: Apr. 7, 2021

(65) Prior Publication Data

US 2022/0322739 A1     Oct. 13, 2022

(51) Int. Cl.
| | |
|---|---|
| *A24F 19/10* | (2006.01) |
| *A24F 19/00* | (2006.01) |
| *A61L 9/12* | (2006.01) |
| *A61L 9/14* | (2006.01) |
| *B60N 3/08* | (2006.01) |

(52) U.S. Cl.
CPC .......... *A24F 19/0042* (2013.01); *A24F 19/10* (2013.01); *A61L 9/127* (2013.01); *A61L 9/14* (2013.01); *B60N 3/083* (2013.01); *A61L 2209/13* (2013.01)

(58) Field of Classification Search
CPC ............ A61L 9/14; A61L 11/00; B60N 3/083
See application file for complete search history.

(56) References Cited

U.S. PATENT DOCUMENTS

| | | | |
|---|---|---|---|
| 3,753,441 A * | 8/1973 | Bennett ................. | A24F 19/025 383/88 |
| 6,070,591 A | 6/2000 | Bryer | |
| 2021/0061526 A1* | 3/2021 | Wisniewski ....... | B65D 47/0809 |

FOREIGN PATENT DOCUMENTS

| | | | |
|---|---|---|---|
| FR | 2138550 A1 | | 1/1973 |
| JP | S63-191197 | * | 12/1988 |
| JP | 2008194446 | * | 8/2008 |
| KR | 10-2011-0138434 | * | 12/2011 |

OTHER PUBLICATIONS

English Translation of JP 2008194446 Tanaka et al. Aug. 2008. (Year: 2008).*
English Translation of FR2138550 Prest (Year: 1971).*
English Machine Translation of Lee et al. KR 10-2011-0138434 (Year: 2011).*
English translation of JP S63-191197 Yoshizumi (Year: 1988).*

* cited by examiner

*Primary Examiner* — Donald R Spamer
(74) *Attorney, Agent, or Firm* — Adibi IP Group, PC; Amir V. Adibi; Andrew C. Palmer

(57) ABSTRACT

A portable scent dispensing ashtray includes an enclosure and a lid. The enclosure comprises an ash retaining portion, an absorbent retaining portion, and a dispenser retaining portion. An absorbent is retained by the absorbent retaining portion. A dispenser is retained by the dispenser retaining portion and stores odor neutralizing matter that is to be absorbed by the absorbent. The lid is rotatably attached to an upper end of the enclosure such that the lid opens or closes. When the lid opens, the ash retaining portion is exposed allowing ash or waste to be deposited into or removed from the ash retaining portion. When the lid closes, the lid activates the dispenser causing the odor neutralizing matter to be released and absorbed by the absorbent. The ashtray is portable and fits into any standard cup holder. The ashtray automatically provides odor neutralization without having to carry a separate odor neutralizing spray.

17 Claims, 14 Drawing Sheets

ASHTRAY 10

PERSPECTIVE VIEW OF ASHTRAY

CROSS SECTIONAL VIEW OF ASHTRAY

ASHTRAY
10

13

18

32

PERSPECTIVE VIEW OF ASHTRAY

FRONT PERSPECTIVE VIEW OF ASHTRAY

ASHTRAY
10

HEIGHT
34

DIAMETER
35

SIDE VIEW OF ASHTRAY

TOP VIEW OF ASHTRAY

12

FRONT VIEW OF ASHTRAY
(LID CLOSED)

ASHTRAY
10

TOP VIEW OF ASHTRAY
(LID CLOSED)

CROSS SECTIONAL VIEW OF ASHTRAY
(ANOTHER EMBODIMENT)

ASHTRAY
50

73

SIDE VIEW OF ASHTRAY

TOP VIEW OF ASHTRAY

FRONT VIEW OF ASHTRAY

ASHTRAY
50

BOTTOM VIEW OF ASHTRAY

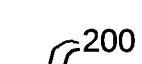

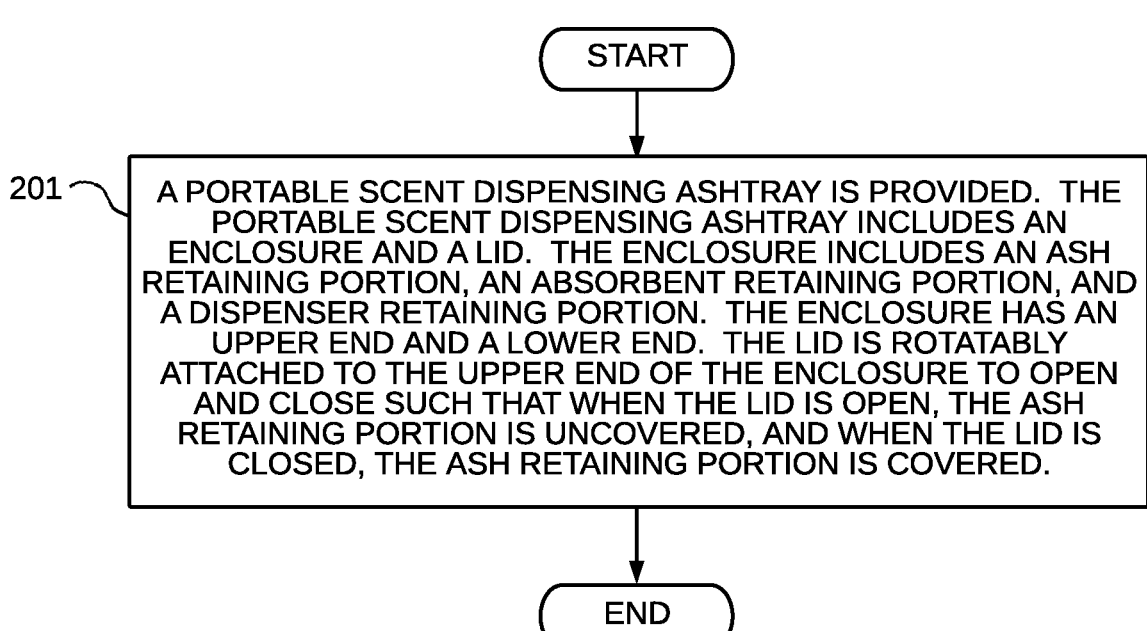

201

```
           ┌─────────┐
           │  START  │
           └────┬────┘
                │
                ▼
┌──────────────────────────────────────────┐
│ A PORTABLE SCENT DISPENSING ASHTRAY IS     │
│ PROVIDED.  THE PORTABLE SCENT DISPENSING   │
│ ASHTRAY INCLUDES AN ENCLOSURE AND A LID.   │
│ THE ENCLOSURE INCLUDES AN ASH RETAINING    │
│ PORTION, AN ABSORBENT RETAINING PORTION,   │
│ AND A DISPENSER RETAINING PORTION.  THE    │
│ ENCLOSURE HAS AN UPPER END AND A LOWER     │
│ END.  THE LID IS ROTATABLY ATTACHED TO THE │
│ UPPER END OF THE ENCLOSURE TO OPEN AND     │
│ CLOSE SUCH THAT WHEN THE LID IS OPEN, THE  │
│ ASH RETAINING PORTION IS UNCOVERED, AND    │
│ WHEN THE LID IS CLOSED, THE ASH RETAINING  │
│ PORTION IS COVERED.                        │
└──────────────────┬─────────────────────────┘
                   │
                   ▼
             ┌─────────┐
             │   END   │
             └─────────┘
```

PORTABLE SCENT DISPENSING ASHTRAY

TECHNICAL FIELD

The present invention relates generally to smoking accessories, and more specifically, to odor neutralizing smoking accessories.

BACKGROUND INFORMATION

Ashtrays are containers commonly used to store ash generated during smoking of cigarettes or cigars. Ashtrays are typically made of glass, metal, or other heat-resistant materials. Typical ashtrays have an opening and a flat base. During smoking, ashes and other waste are deposited into the opening of the ashtray. The waste is stored within the ashtray until being emptied into a rubbish bin.

SUMMARY

A portable scent dispensing ashtray includes an enclosure and a lid. The enclosure comprises an ash retaining portion, an absorbent retaining portion, and a dispenser retaining portion. An absorbent is retained by the absorbent retaining portion. A dispenser is retained by the dispenser retaining portion and stores odor neutralizing matter that is to be absorbed by the absorbent. The lid is rotatably attached to an upper end of the enclosure via a hinge such that the lid opens or closes. When the lid opens, the ash retaining portion is exposed allowing ash or waste to be deposited into or removed from the ash retaining portion. When the lid closes, the lid activates the dispenser causing the odor neutralizing matter to be released and absorbed by the absorbent.

The ashtray is highly portable and fits into any standard cup holder. In one example, a user enters a vehicle with the novel ashtray and places the ashtray in a cup holder of the vehicle. Next, the user opens the lid of the ashtray. During the vehicle ride, the user smokes a cigarette and deposits ash into the ashtray. After the user is done smoking, the remaining cigarette and ashes are deposited into the ashtray. The user closes the lid thereby activating the dispenser and causing the odor neutralizing material to be released by the dispenser and absorbed by the absorbent. The odor neutralizing material dissipates throughout the vehicle and helps neutralize undesirable odors generated during smoking of the cigarette. The ashtray automatically provides odor neutralization without having to carry a separate odor neutralizing spray. Once the user reaches their destination, the user exits the vehicle with the ashtray. The ashtray can be placed within personal baggage without concern with waste or ash stored in the ashtray falling out. Once the user reaches a trash bin, the user opens the lids and disposes of waste and ash collected within the ashtray.

In accordance with one novel aspect, the ashtray has a height that is at least one and a half times the diameter. These novel dimensions provide optimal ash retaining and scent dispensing capabilities while ensuring the ashtray remains highly portable and fits into standard cup holders, such as vehicle cup holders. The novel ashtray is formed from heat resistant materials. In one embodiment, the ashtray is formed from entirely mechanical components and does not include any electronics requiring energy storage or conversion. In another embodiment, the ashtray is formed from injection molded plastic. In still another embodiment, the ashtray is machined from metallic materials. In yet another embodiment, the ashtray is formed via an additive manufacturing process such as a three-dimensional printing process.

Further details and embodiments and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 14 is a flowchart of a method 200 in accordance with another novel aspect.

DETAILED DESCRIPTION

Reference will now be made in detail to some embodiments of the invention, examples of which are illustrated in the accompanying drawings.

Figure 1:
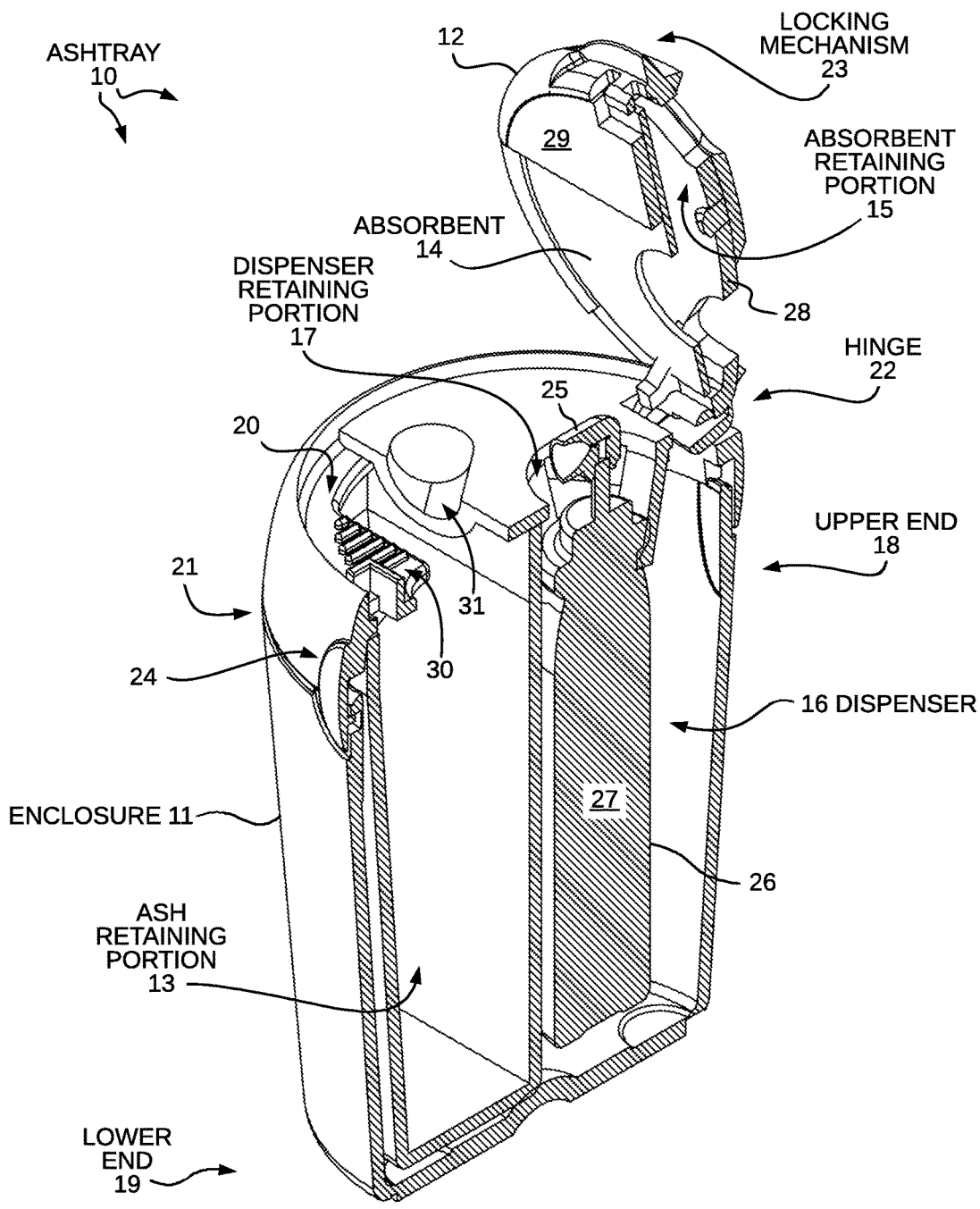
FIG. 1 is a diagram of a cross sectional view of an ashtray 10.

FIG. 1 is a diagram of a cross sectional view of an ashtray 10. The ashtray 10 is a portable scent dispensing ashtray that fits into any cup holder, such as a vehicle cup holder. The ashtray 10 comprises an enclosure 11 and a lid 12. The enclosure 11 comprises an ash retaining portion 13, an absorbent 14, an absorbent retaining portion 15, a dispenser 16, and a dispenser retaining portion 17. The enclosure 11 has an upper end 18, a lower end 19, an interior 20, and an exterior 21.

The lid 12 provides access to the interior 20 of the enclosure 11. The lid 12 is rotatably attached to the upper end 18 of the enclosure 11 via a hinge 22. The lid 12 is rotated open or rotated closed about the hinge 22. The lid 12 includes a locking mechanism 23 that engages with a locking mechanism 24 of the enclosure 11. When the lid 12 is open, the ash retaining portion 13 is uncovered. This allows material or waste to be deposited into or removed from the ash retaining portion 13. When the lid 12 is closed, the lid 12 activates the dispenser releasing scented material into the absorbent 14. After the lid 12 is closed, the ash retaining portion 13 is covered. This prevents material or waste deposited in the ash retaining portion 13 from undesirably falling out of the ashtray 10 thereby contributing to portability and convenience of ashtray 10.

In this embodiment, the locking mechanisms 23 and 24 involve a button that causes a latch to be released thereby allowing the lid 12 to swing open. In another embodiment, the locking mechanisms 23 and 24 involve a motion detector that causes the lid 12 to open in response to detecting motion by a user near the ashtray 10, such as waving a hand over the ashtray 10. In yet another embodiment, the locking mechanisms 23 and 24 involve a heat detector that causes the lid 12 to open in response to detecting heat of a lit cigarette near the ashtray 10. In still another embodiment, the locking mechanisms 23 and 24 involve an auditory detector that causes the lid 12 to open in response to audio input, such as a voice command from a user. In yet another embodiment, the ashtray 10 includes an IoT (Internet of Things) wireless controller and the locking mechanisms 23 and 24 are remotely controlled via a remote control, mobile device, or virtual assistant that causes the lid 12 to open in response to a wireless signal.

The ash retaining portion 13 extends from the upper end 18 of the enclosure 11 to the lower end 19 of the enclosure 11. The ash retaining portion 13 receives and stores ash or other waste deposited into the ashtray by a user. In one example, the ash retaining portion 13 is a removable container that fits within the enclosure 11. In another example, the ash retaining portion 13 is a fixed compartment within the enclosure 11 having sidewalls.

The dispenser retaining portion 17 receives the dispenser 16. The dispenser retaining portion 17 provides an opening that maintains the dispenser 16 in a position within the interior 20 of the enclosure 11 thereby ensuring that the dispenser 16 is activated upon closure of the lid 12. In some embodiments, the dispenser retaining portion 17 includes a mechanical retention mechanism that accepts and retains the dispenser 16. Such mechanical retention mechanisms include one or more grooves, hooks, clips, latches, connectors, or any suitable mechanical attachments. In one embodiment, the dispenser retaining portion 17 includes a key or guide that ensures only specialized dispensers manufactured for the ashtray 10 are accepted into the enclosure 11.

The dispenser 16 comprises a trigger activated spray valve 25 and a container 26 that stores material 27. In one embodiment, the spray valve 25 is a one-way valve. When the spray valve 25 is pressed down, the material 27 stored in the container 26 is released out of the spray valve 25. In this embodiment, the material is a scented spray 27 that reduces undesirable olfactory characteristics of the surrounding environment. For example, the scented spray 27 at least partially neutralizes unwanted odors caused by burning cigarettes, cigars, or other materials or substances. The spray valve 25 is activated by a user pressing the lid 12 shut thereby causing the lid 12 to activate the spray valve 25. The spray valve 25 is also activated by a user pressing directly down on the spray valve 25 when the lid 12 is open.

The dispenser 16 is any suitable dispenser that is activatable in response to closure of the lid 12. The dispenser 16 is designed to extract liquid 27 from container 26 using the spray valve 25 and spring. The dispenser 16 forces the liquid 27 through spray valve 25 converting the liquid into a fine mist or stream. Alternatively, pressurized air is optionally used to propel the liquid 27 out of the container 26. Certain details of dispenser 16 are intentionally omitted.

The absorbent 14 is any suitable material that stores or retains scented material that is stored and emitted by the dispenser 16. The absorbent 14 is retained by the absorbent retaining portion 15. In this example, the absorbent retaining portion 15 is formed between surfaces 28 and 29 of the lid. The absorbent 14 is disposed and held in place between the surfaces 28 and 29 of the lid. In one embodiment, the absorbent 14 is fixed. In another embodiment, the absorbent 14 is removable and replaceable with a new absorbent. During operation, the lid 12 is closed thereby pressing down on the nozzle 25 dispenser 16 causing the dispenser 16 to dispense the scented spray into the absorbent 14. In one example, the absorbent 14 is a cellulose fiber material such as paper or fabric.

The enclosure 11 includes features 30 and 31 within the interior 20 that provide additional functionality to a user of the ashtray 10. Feature 30 is a plurality of ridges. Feature 31 is a groove. Each of features 30 and 31 provides a support surface or a brushing surface. For example, features 30 and 31 are usable to rest a burning cigarette or to brush ashes from an end of a burning cigarette.

Figure 2:
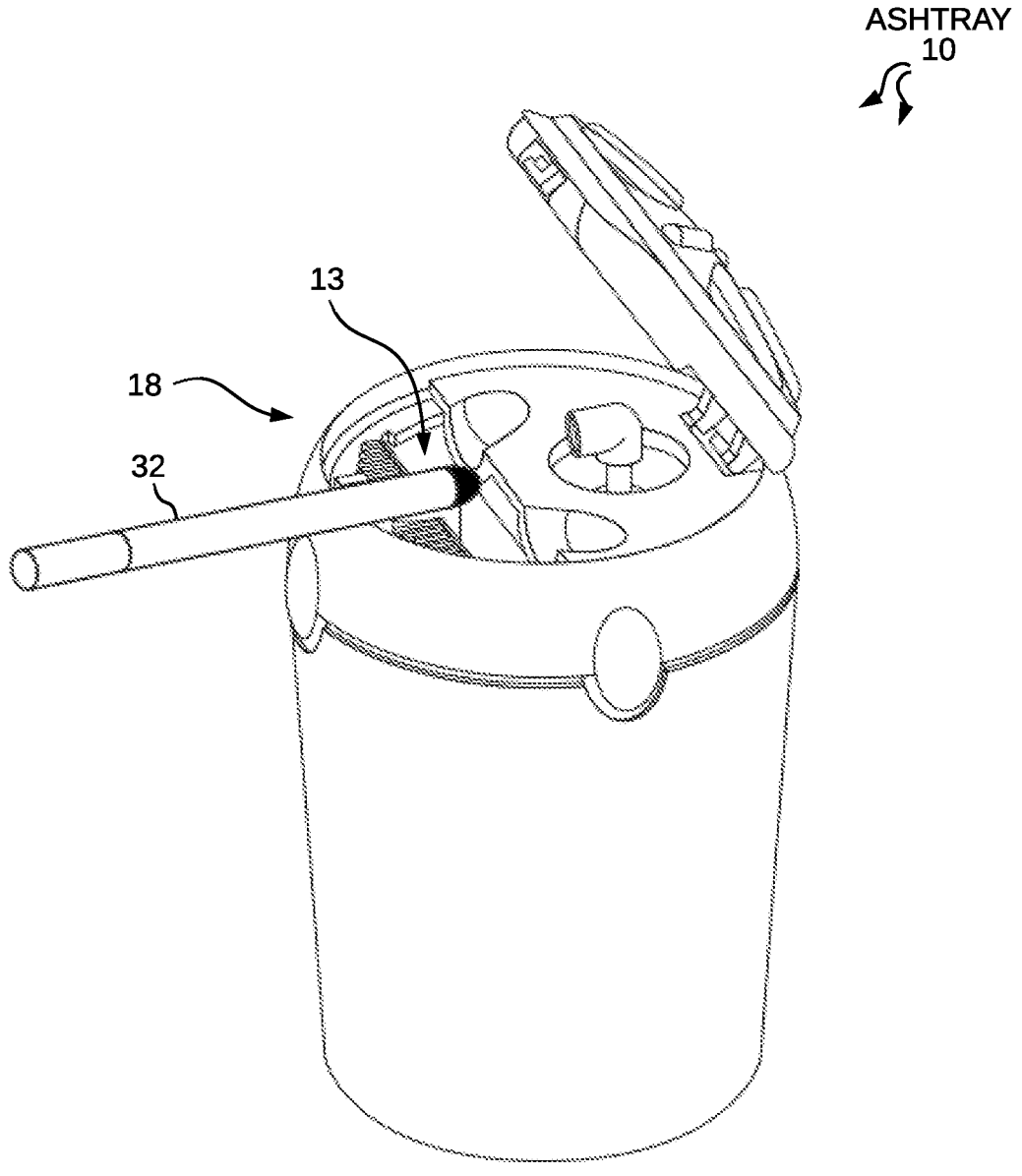
FIG. 2 is a diagram showing a side perspective view of a cigarette 32 depositing ash into the ashtray 10.

FIG. 2 is a diagram showing a side perspective view of a cigarette 32 depositing ash into the ashtray 10. The cigarette 32 is struck against the upper end 18 of the ashtray 10 causing ash from the cigarette 32 to fall into the ash retaining portion 13.

Figure 3:
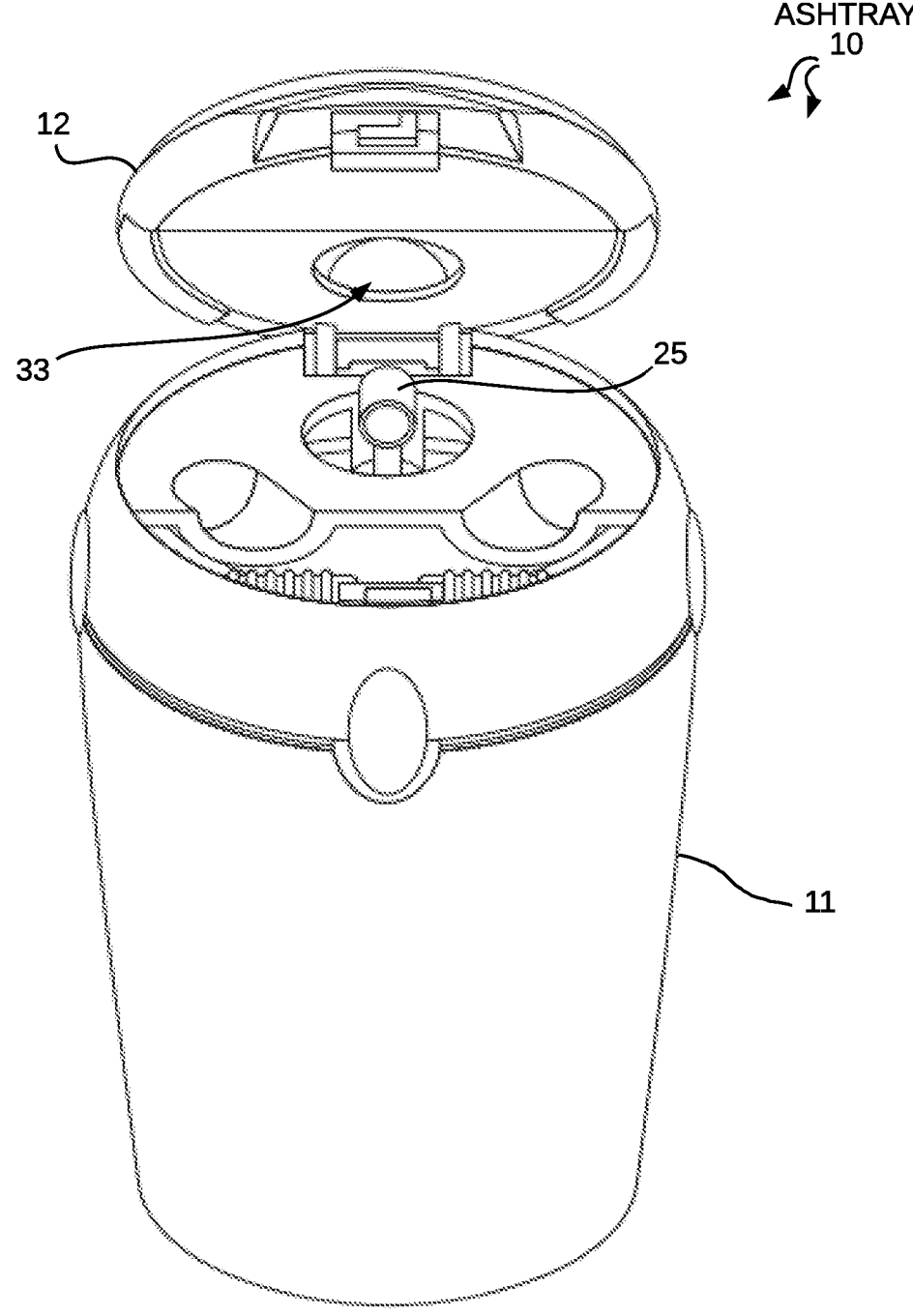
FIG. 3 is a diagram showing a front perspective view of the ashtray 10.

FIG. 3 is a diagram showing a front perspective view of the ashtray 10. As the lid 12 is pressed down, the spray nozzle 25 extends through opening 33 and contacts surface 28 of the lid 12. Surface 28 of the lid 12 presses down on the spray nozzle 25 causing the dispenser 16 to release scented spray. The scented spray is absorbed by absorbent 14. In this way, the ashtray 10 contributes to neutralizing undesirable odors produced by smoke, cigarettes, and cigars without a user having to deliberately spray scents or odor neutralizing sprays. The odor neutralization provided by the ashtray 10 is conveniently integrated into the enclosure 11 and dispersed automatically after each closure of the lid 12.

Figure 4:
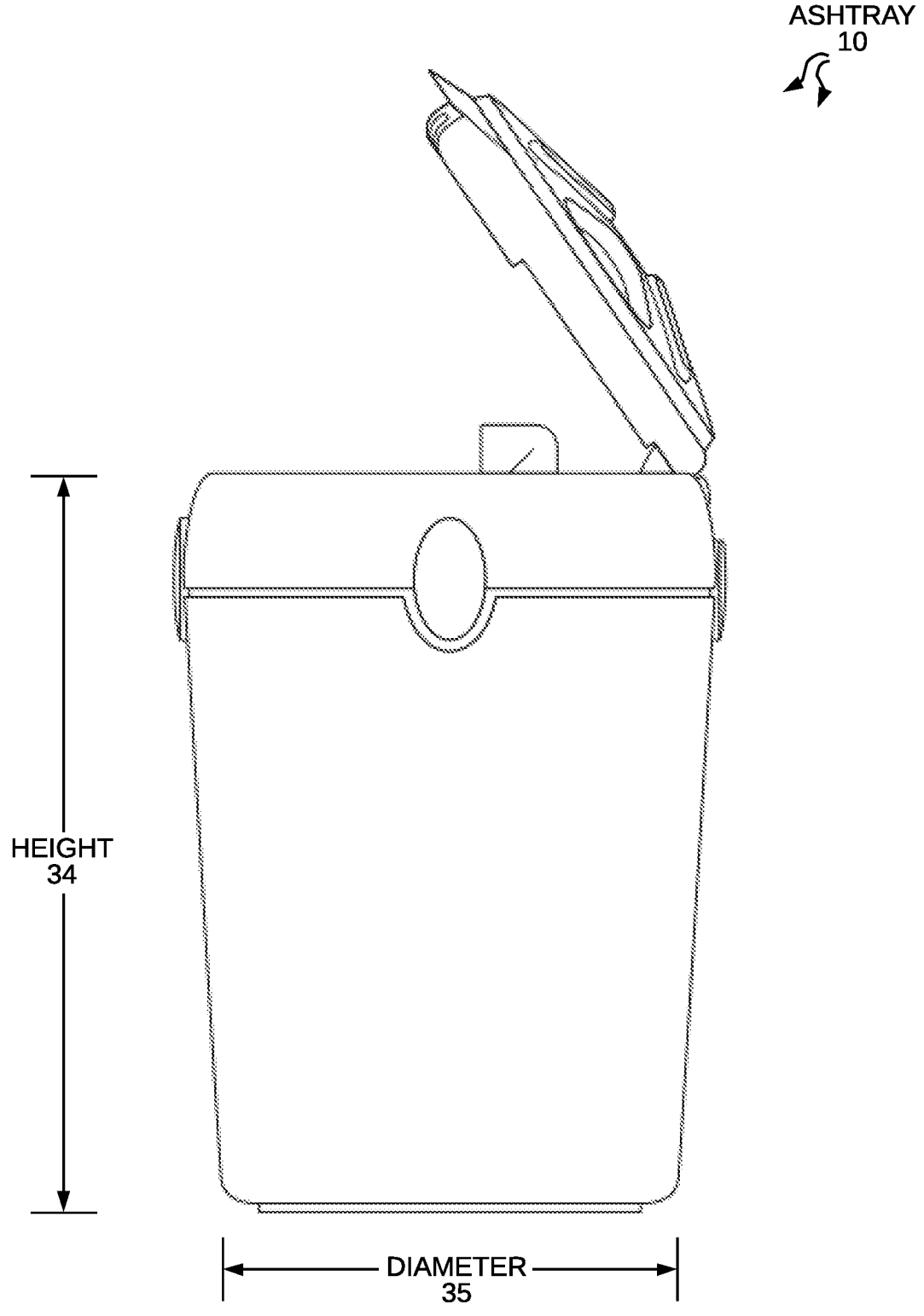
FIG. 4 is a diagram showing a side view of the ashtray 10.

FIG. 4 is a diagram showing a side view of the ashtray 10. The enclosure 11 has a height 34 and a diameter 35. In one embodiment, the height 34 is at least one and a half times the diameter 35 thereby providing optimal ash retaining and scent dispensing capabilities while ensuring the ashtray 10 is highly portable and fits into cup holders, including vehicle cup holders. The diameter 35 is configured to fit into standard cup holders. In one example, the diameter 35 is at least two inches. In the embodiment shown in FIG. 4, the height 34 is 4.5 inches and the diameter 35 is 2.9 inches.

Figure 5:
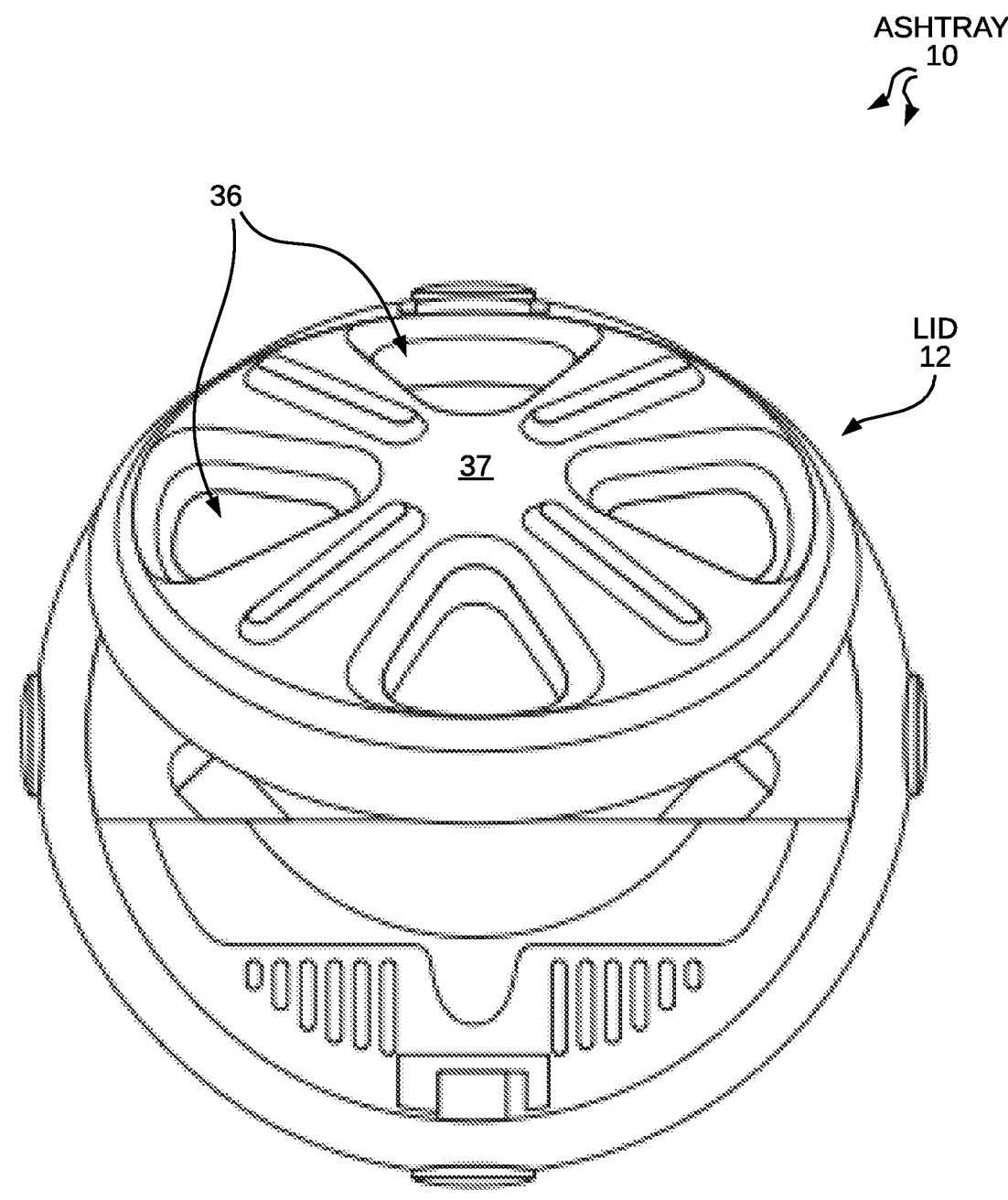
FIG. 5 is a diagram showing a top view of the ashtray 10 when the lid 12 is open.

FIG. 5 is a diagram showing a top view of the ashtray 10 when the lid 12 is open. A plurality of openings 36 is provided in the lid 12. The openings 36 expose the absorbent 14 to the exterior 21 of the enclosure 11. Exposing the absorbent 14 to the outside helps release neutralizing scents emitted by the dispenser 16 and captured by the absorbent 14 after the lid 12 is closed. In this embodiment, the lid 12 comprises a top cover 37. The top cover 37 rotates exposing openings 36 or closing off openings 36. In another embodiment, the top cover 37 is not rotatable and the openings 36 always remain open. In yet another embodiment, the lid 12 has no openings 36.

Figure 6:
FIG. 6 is a diagram showing a top perspective view of the ashtray 10 after the lid 12 is closed.
Figure 6:
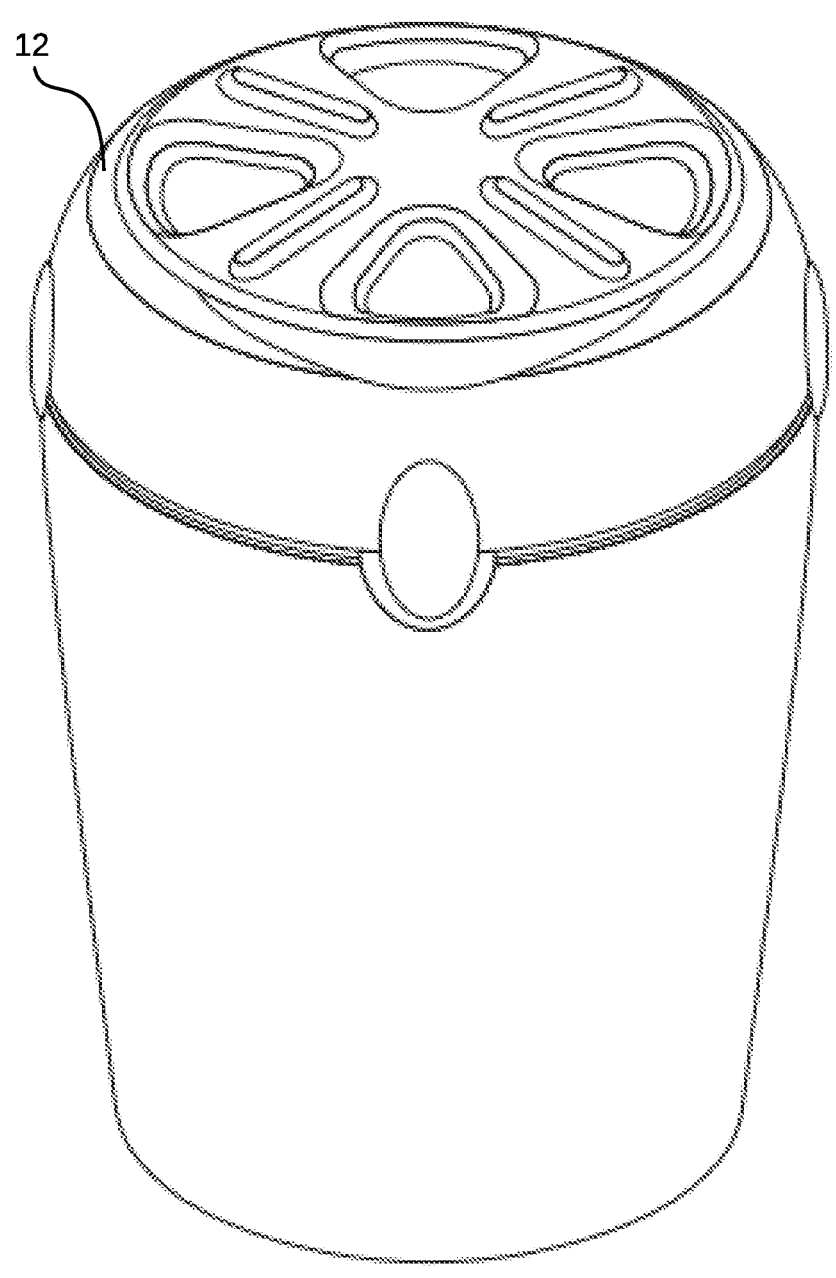

FIG. 6 is a diagram showing a top perspective view of the ashtray 10 after the lid 12 is closed.

Figure 7:
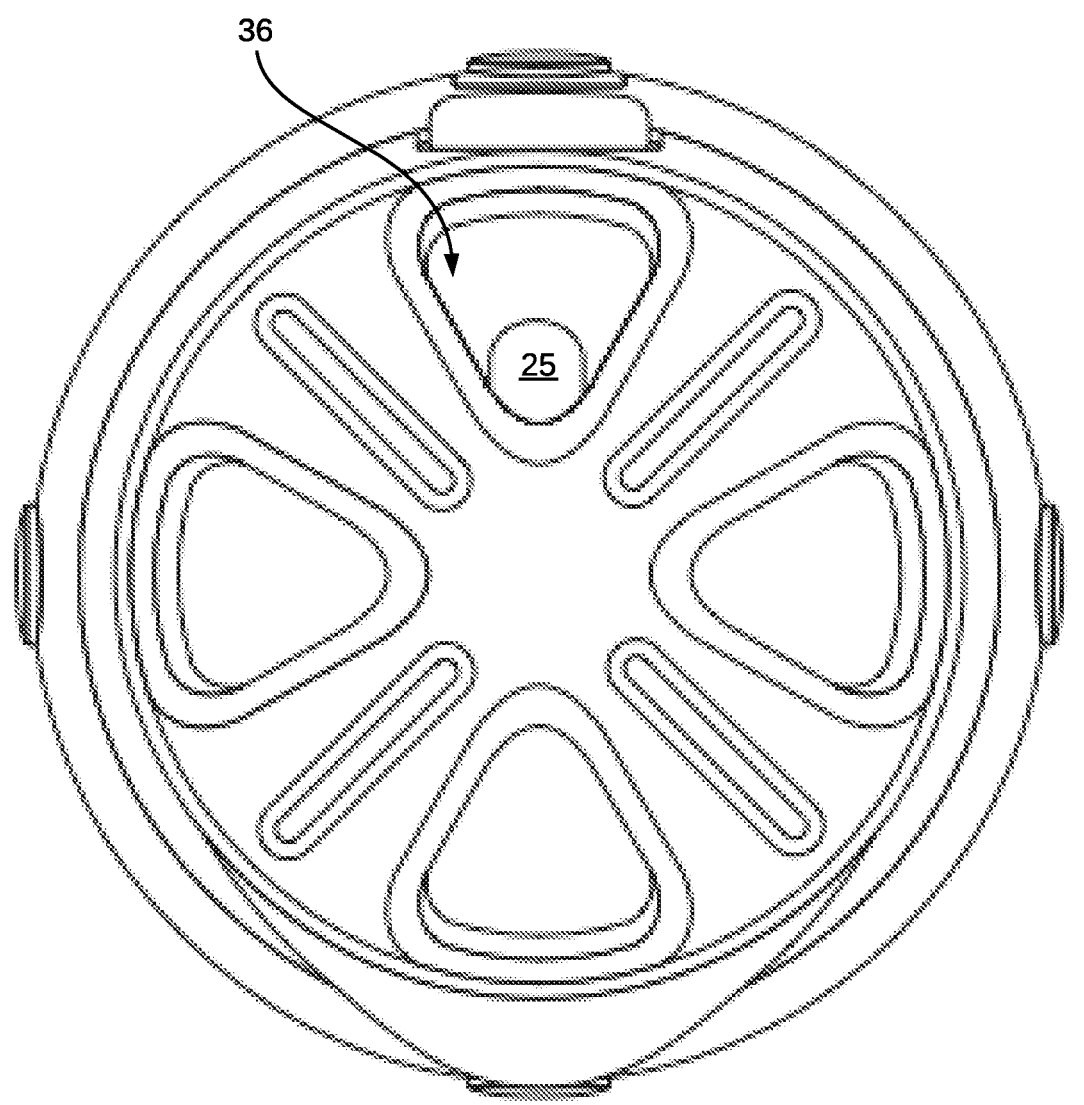
FIG. 7 is a diagram showing a top view of the ashtray 10 after the lid 12 is closed.

FIG. 7 is a diagram showing a top view of the ashtray 10 after the lid 12 is closed. A portion of the spray nozzle 25 of the dispenser is visible through openings 36 of the lid 12.

Figure 8:
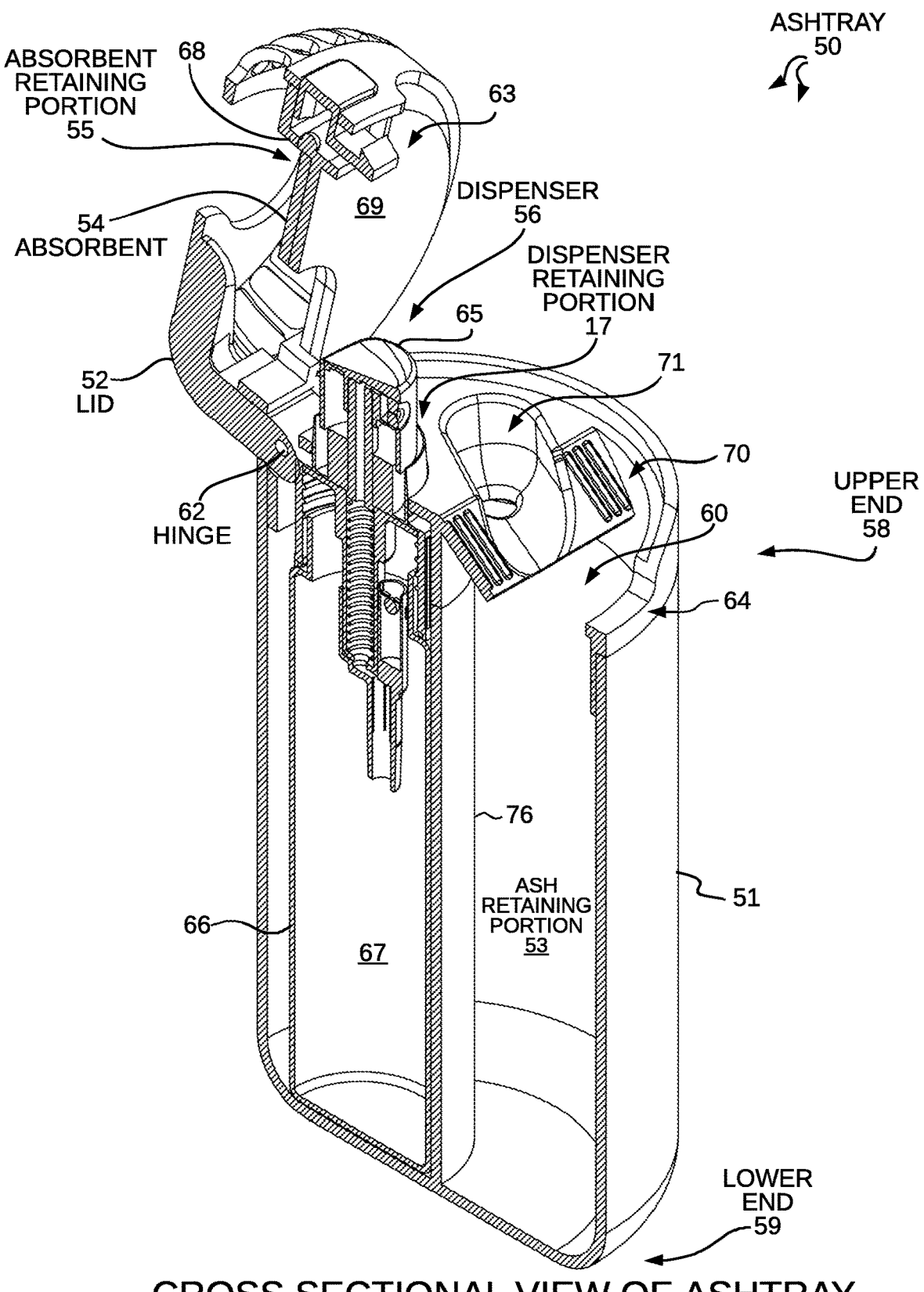
FIG. 8 is a diagram showing a cross sectional view of another embodiment of a novel ashtray 50.

FIG. 8 is a diagram showing a cross sectional view of another embodiment of a novel ashtray 50. The ashtray 50 is a portable scent dispensing ashtray that fits into any standard cup holder. The ashtray 50 comprises an enclosure 51 and a lid 52. The lid 52 includes openings that remain open and are not provided with functionally that allows a user to optionally close the openings. The enclosure 51 comprises an ash retaining portion 53, an absorbent 54, an absorbent retaining portion 55, a dispenser 56, and a dispenser retaining portion 57. The enclosure 51 has an upper end 58, a lower end 59, an interior 60, and an exterior 61.

The lid 52 provides access to the interior 60 of the enclosure 51. The lid 52 is rotatably attached to the upper end 58 of the enclosure 51 via a hinge 62. The lid 52 is rotated open or rotated closed about the hinge 62. The lid 52 includes a locking mechanism 63 that engages with a locking mechanism 64 of the enclosure 51. When the lid 52 is open, the ash retaining portion 53 is uncovered. This allows material or waste to be deposited into or removed from the ash retaining portion 53. When the lid 52 is closed, the lid 52 activates the dispenser releasing scented material into the absorbent 54. After the lid 52 is closed, the ash retaining portion 53 is covered. This prevents material or waste deposited in the ash retaining portion 53 from undesirably falling out of the ashtray 50 thereby contributing to portability and convenience of ashtray 50. The locking mechanisms 53 and 54 involve any suitable locking mechanism including mechanical or wireless mechanisms described in connection with ashtray 10.

The ash retaining portion 53 extends from the upper end 58 of the enclosure 51 to the lower end 59 of the enclosure 51. The ash retaining portion 53 receives and stores ash or other waste deposited into the ashtray by a user. In one example, the ash retaining portion 53 is a removable container that fits within the enclosure 51. In another example, the ash retaining portion 53 is a fixed compartment within the enclosure 51 having sidewalls. A wall 76 separates the ash retaining portion 53 from the dispenser retaining portion 57.

The dispenser retaining portion 57 receives the dispenser 56. The dispenser retaining portion 57 provides an opening that maintains the dispenser 56 in a position within the interior 60 of the enclosure 51 thereby ensuring that the dispenser 56 is activated upon closure of the lid 52. In some embodiments, the dispenser retaining portion 57 includes a mechanical retention mechanism that accepts and retains the dispenser 56. Such mechanical retention mechanisms include one or more grooves, hooks, clips, latches, connectors, or any suitable mechanical attachments. In one embodiment, the dispenser retaining portion 57 includes a key or guide that ensures only specialized dispensers manufactured for the ashtray 50 are accepted into the enclosure 51.

The dispenser 56 comprises a trigger activated spray valve 65 and a container 66 that stores material 67. When the spray valve 65 is pressed down, the material 67 stored in the container 66 is released out of the spray valve 65. In this embodiment, the material is a scented spray 67 that reduces undesirable olfactory characteristics of the surrounding environment. For example, the scented spray 67 partially masks unwanted odors caused by burning cigarettes, cigars, or other materials or substances. The spray valve 65 is activated by a user pressing the lid 52 shut thereby causing the lid 52 to activate the spray valve 65. The spray valve 65 is also activated by a user pressing directly down on the spray valve 65 when the lid 52 is open. The dispenser 56 is any suitable dispenser that is activatable in response to closure of the lid 52. Certain details of dispenser 56 are intentionally omitted.

The absorbent 54 is any suitable material and shape that stores or retains scented material that is stored and emitted by the dispenser 56. In this embodiment, the absorbent 54 has a circular shape with an opening at a center. This donut-like shape matches the lid 52 and opening provided for passage of the spray valve 65. In one example, the absorbent 54 is a cellulose fiber material such as paper or fabric.

The absorbent 54 is retained by the absorbent retaining portion 55. In this example, the absorbent retaining portion 55 is formed between surfaces 68 and 69 of the lid 52. The absorbent 54 is disposed and held in place between the surfaces 68 and 69 of the lid 52. In one embodiment, the absorbent 54 is fixed. In another embodiment, the absorbent 54 is removable and replaceable with a new absorbent. During operation, the lid 52 is closed thereby pressing down on the nozzle 65 dispenser 56 causing the dispenser 56 to dispense the scented spray into the absorbent 54.

Figure 9:
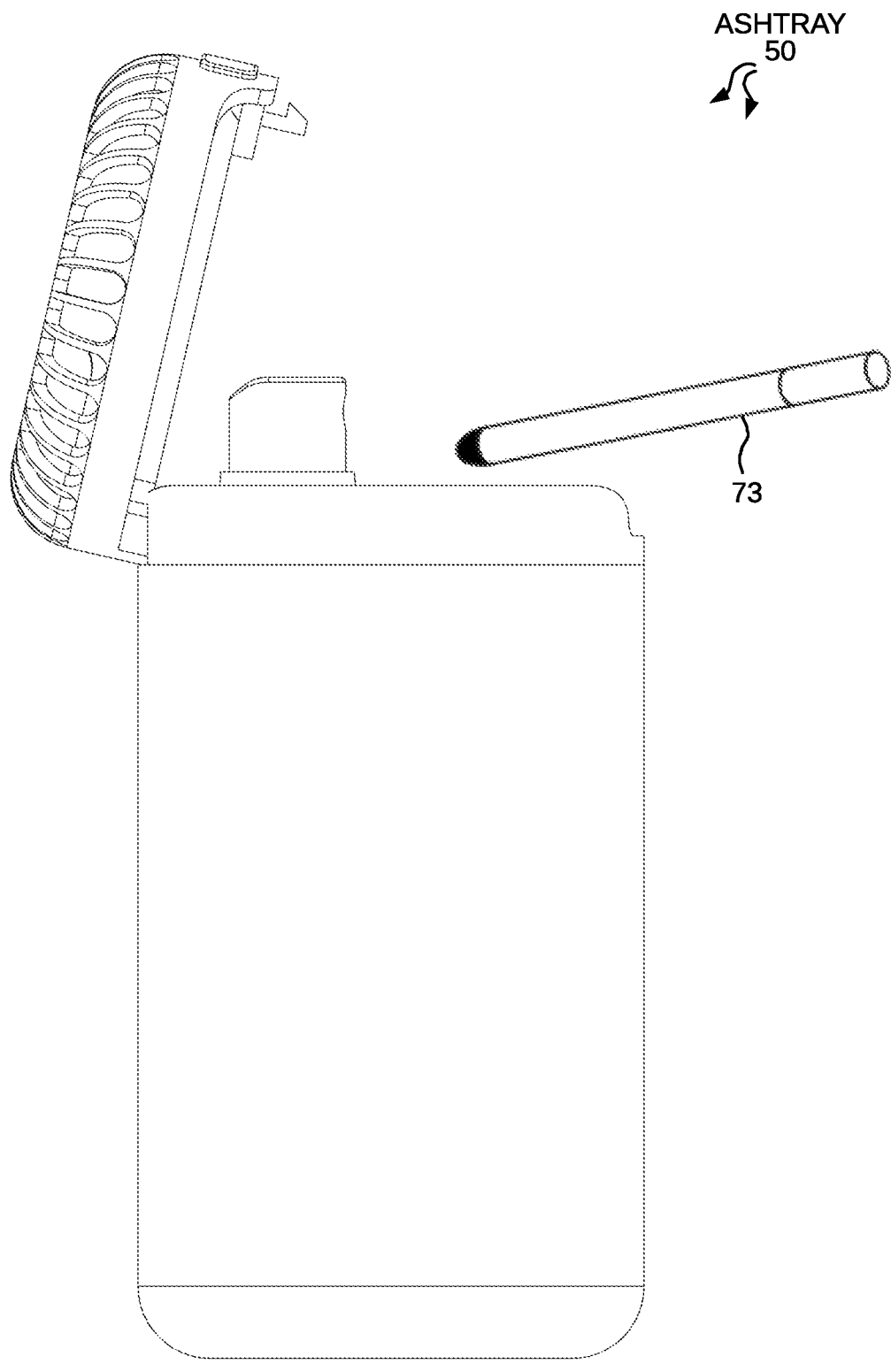
FIG. 9 is a diagram showing a side view of a cigarette 73 depositing ash into the ashtray 50.

FIG. 9 is a diagram showing a side view of a cigarette 73 depositing ash into the ashtray 50.

Figure 10:
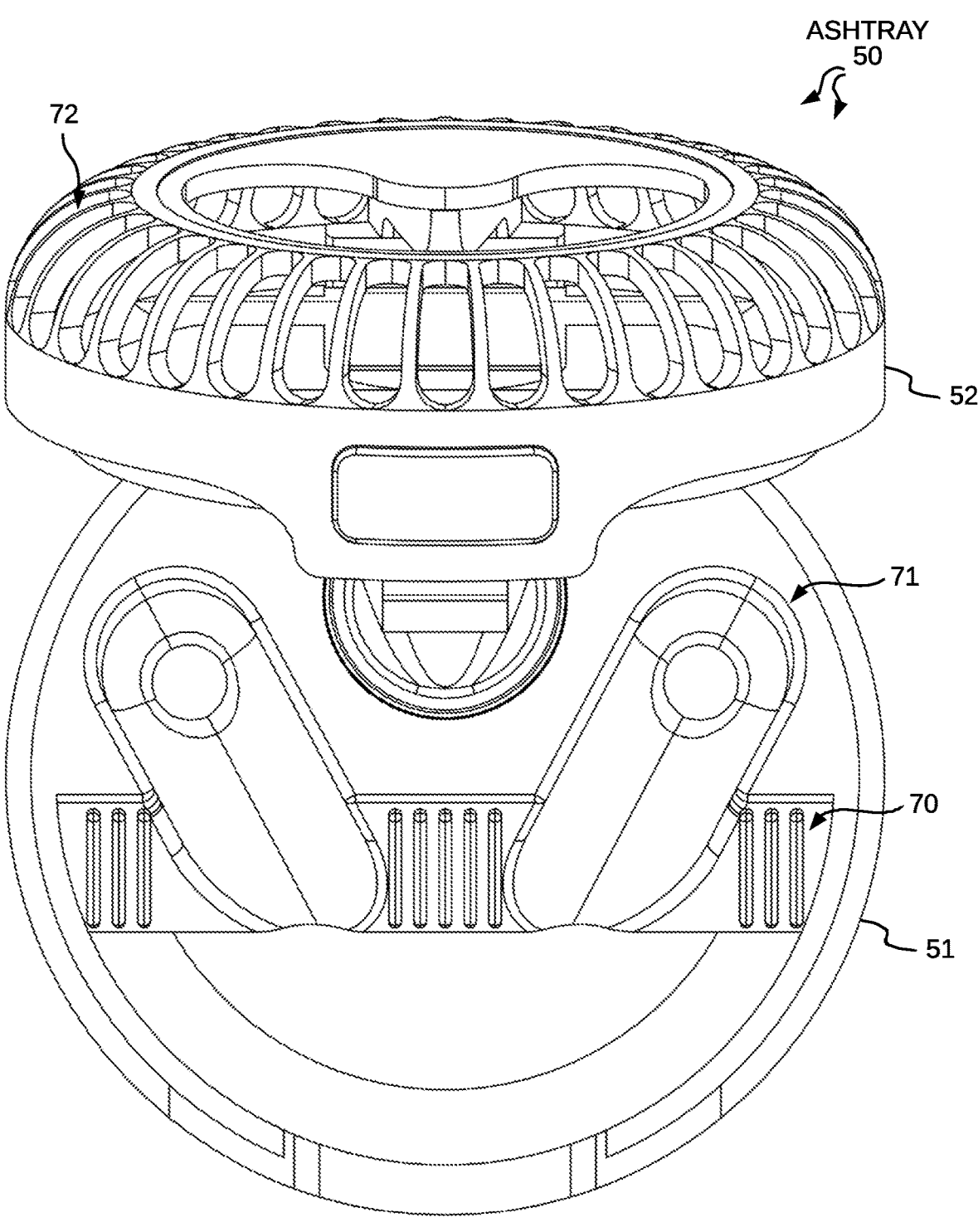
FIG. 10 is a diagram showing a top view of the ashtray 50 when the lid 52 is open.

FIG. 10 is a diagram showing a top view of the ashtray 50 when the lid 52 is open. The enclosure 51 includes features 70 and 71 within the interior 60 that provide additional functionality to a user of the ashtray 50. Feature 70 is a plurality of ridges. Feature 71 is a groove. Each of features 70 and 71 provides a support surface or a brushing surface. For example, features 70 and 71 are usable to rest a burning cigarette or to brush ashes from an end of a burning cigarette.

A plurality of openings 72 is provided in the lid 52. The openings 36 expose the absorbent 54 to the exterior 61 of the enclosure 51. Exposing the absorbent 54 to the outside helps release neutralizing scents emitted by the dispenser 56 and captured by the absorbent 54 after the lid 52 is closed.

Figure 11:
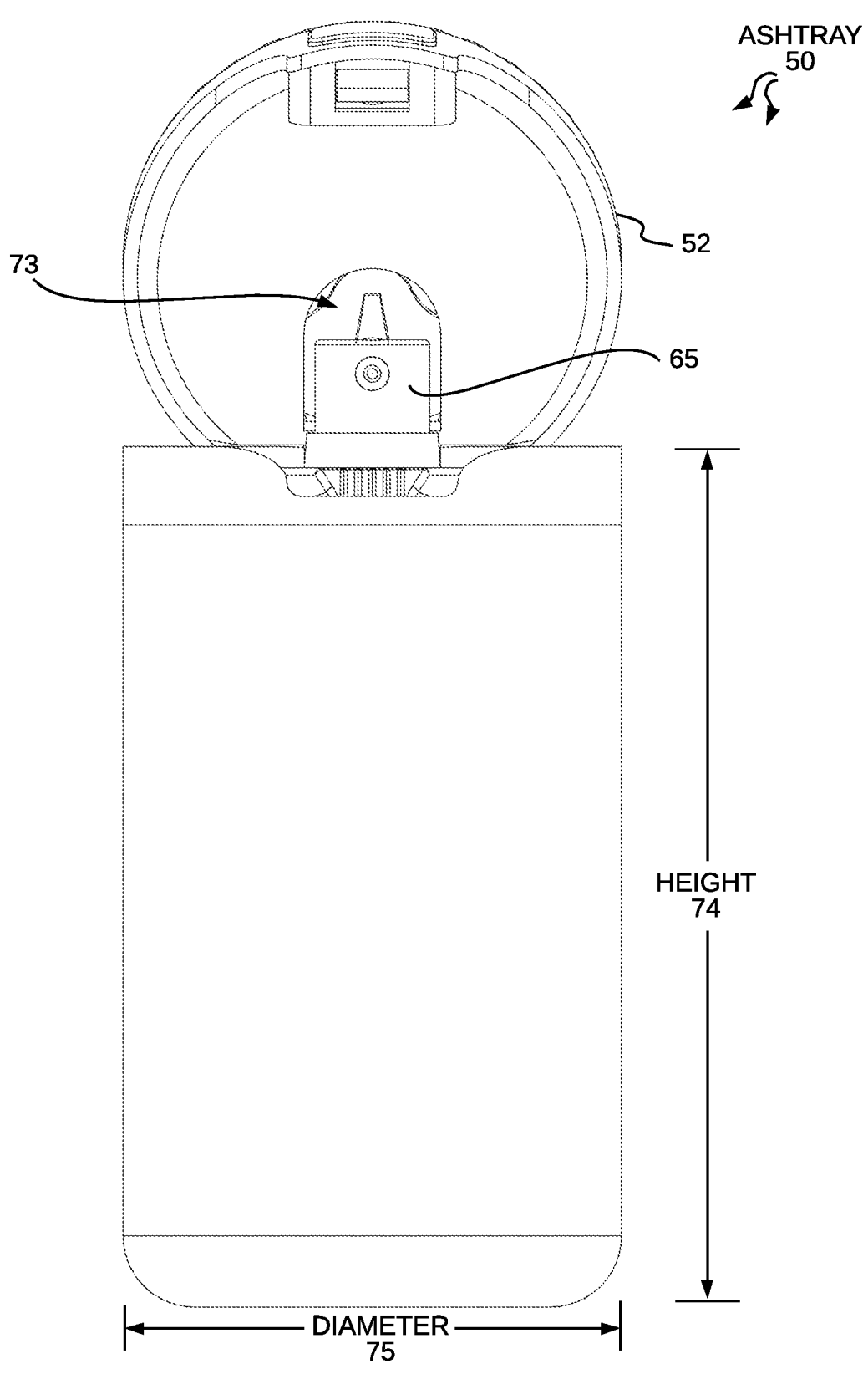
FIG. 11 is a diagram showing a front view of the ashtray 50 when the lid 52 is open.

FIG. 11 is a diagram showing a front view of the ashtray 50 when the lid 52 is open. As the lid 52 is pressed down, the spray nozzle 65 extends through opening 72 and contacts an inner surface of the lid 52. The inner surface of the lid 52 presses down on the spray nozzle 65 causing the dispenser 56 to release scented spray. The scented spray is absorbed by absorbent 54. In this way, the ashtray 50 contributes to neutralizing undesirable odors produced by smoke, cigarettes, and cigars without a user having to deliberately spray scents or odor neutralizing sprays. The odor neutralization provided by the ashtray 50 is conveniently integrated into the enclosure 51 and dispersed automatically after each closure of the lid 52.

The enclosure 51 has a height 74 and a diameter 75. In one embodiment, the height 74 is at least one and a half times the diameter 75 thereby providing optimal ash retaining and scent dispensing capabilities while ensuring the ashtray 50 is highly portable and fits into cup holders, including vehicle cup holders. The diameter 75 is configured to fit into standard cup holders. In one example, the diameter 75 is at least two inches. In the embodiment of ashtray 50, the height 74 is 4.5 inches and the diameter 75 is 2.9 inches.

Figure 12:
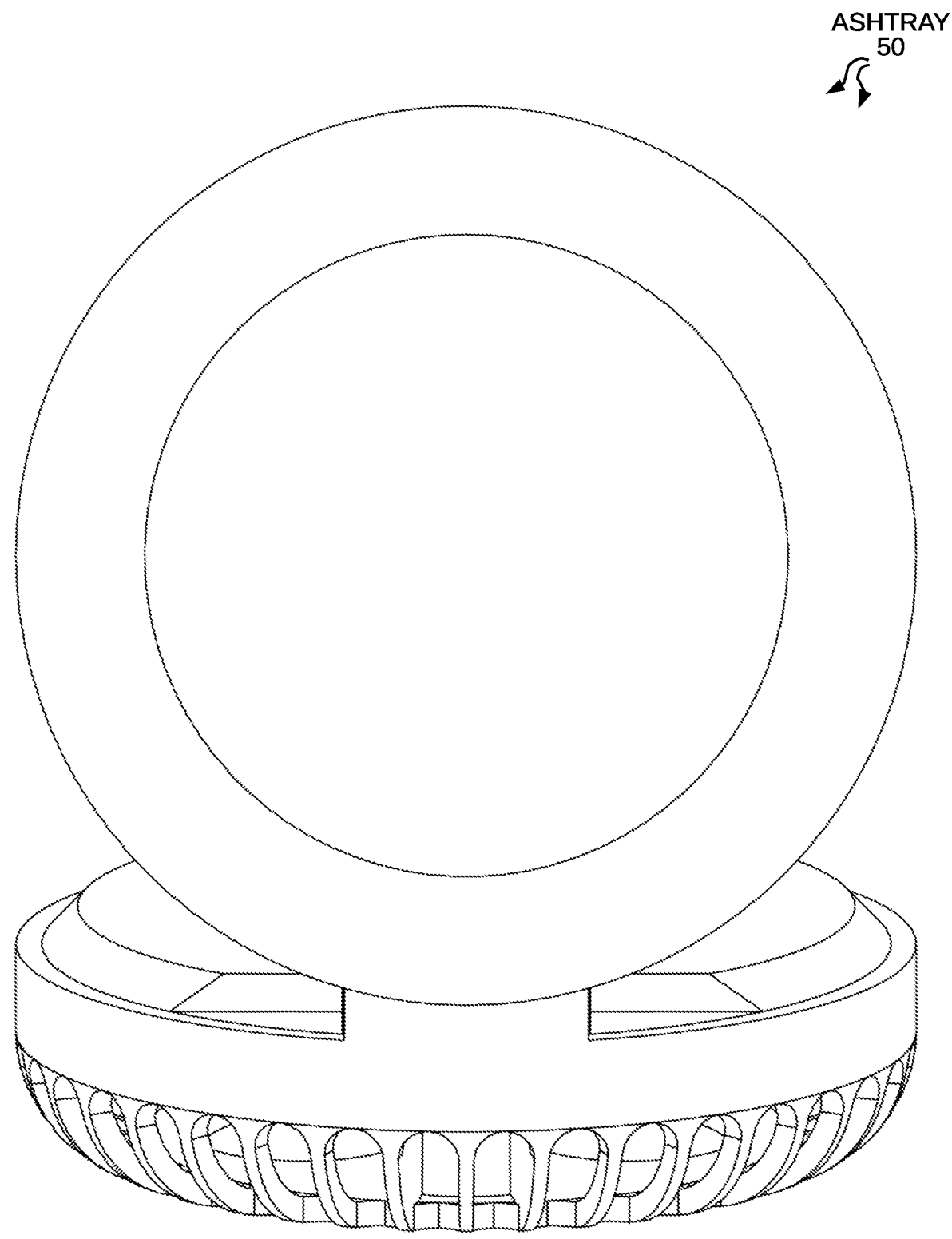
FIG. 12 is a diagram showing a bottom view of the ashtray 50 when the lid 52 is open.

FIG. 12 is a diagram showing a bottom view of the ashtray 50 when the lid 52 is open.

Figure 13:
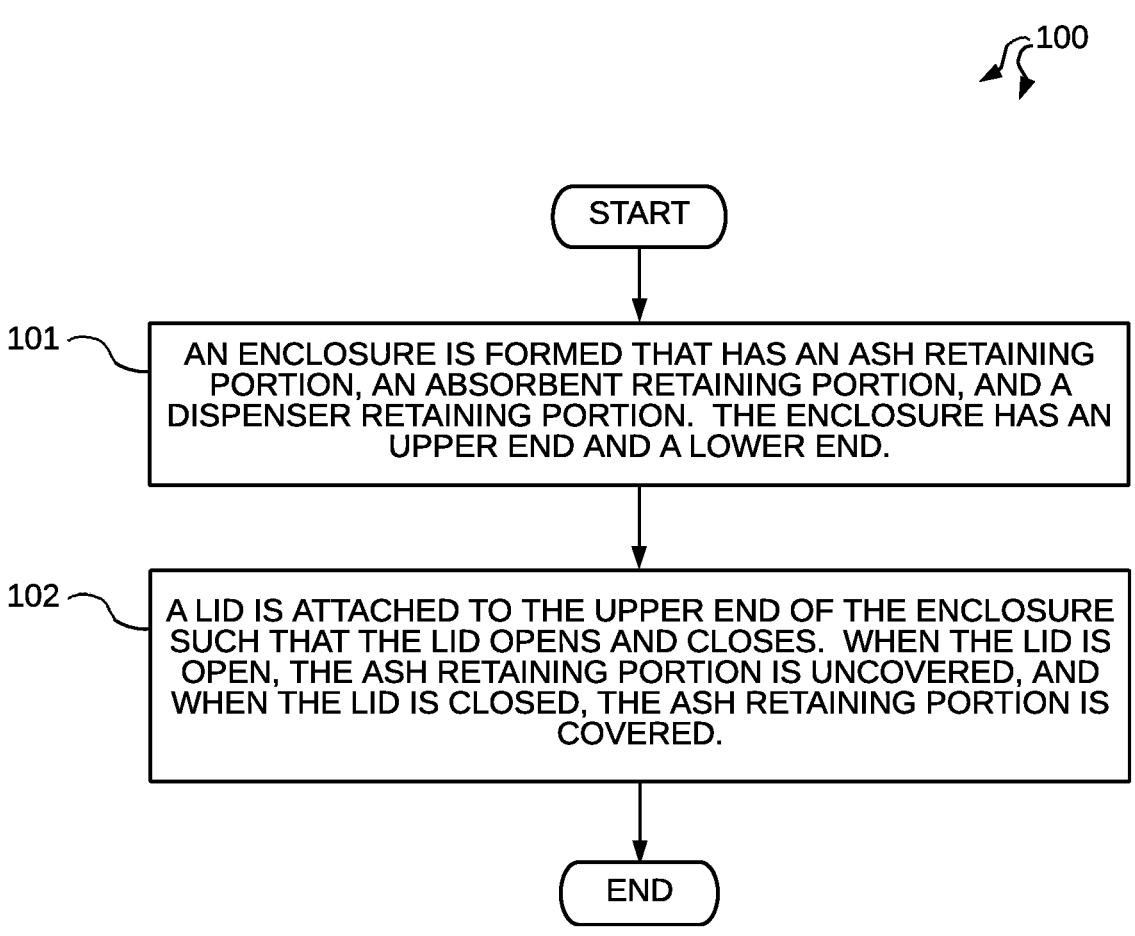
FIG. 13 is a flowchart of a method 100 in accordance with one novel aspect.

FIG. 13 is a flowchart of a method 100 in accordance with one novel aspect. In a first step (step 101), an enclosure is formed having an ash retaining portion, an absorbent retaining portion, and a dispenser retaining portion. The enclosure has an upper end and a lower end.

In a second step (step 102), a lid is attached to the upper end of the enclosure such that the lid opens and closes. When the lid is open, the ash retaining portion is uncovered. When the lid is closed, the ash retaining portion is covered.

FIG. 14 is a flowchart of a method 200 in accordance with another novel aspect. In a first step (step 201), a portable scent dispensing ashtray is provided. The portable scent dispensing ashtray includes an enclosure and a lid. The enclosure comprises an ash retaining portion, an absorbent retaining portion, and a dispenser retaining portion. The enclosure has an upper end and a lower end. The lid is rotatably attached to the upper end of the enclosure to open and close. When the lid is open, the ash retaining portion is uncovered. When the lid is closed, the ash retaining portion is covered.

Although certain specific embodiments are described above for instructional purposes, the teachings of this patent document have general applicability and are not limited to the specific embodiments described above. The lid is shown connected to the enclosure in various embodiments via a hinge, however, in other embodiments, the lid is attached to the enclosure through a malleable or flexible attachment that allows the lid to open and close. Even though the figures show the dispenser disposed within the dispenser retaining portion and the absorbent within the absorbent retaining portion, it is appreciated that one entity might manufacture and provide the ashtray without the absorbent or the dispenser. The manufacturing entity might then provide the novel ashtray to one or more entities that later incorporate the absorbent or the dispenser into the ashtray. It is also appreciated that the absorbent or the dispenser might be especially manufactured and designed to fit the novel ashtray and sold to consumers as refillable accessories that are to be installed by end consumers. Accordingly, various modifications, adaptations, and combinations of various features of the described embodiments can be practiced without departing from the scope of the invention as set forth in the claims.

What is claimed is:

1. An apparatus comprising:
an enclosure having an ash retaining portion, an absorbent retaining portion, and a dispenser retaining portion, wherein the enclosure has an upper end and a lower end, and wherein the ash retaining portion is accessible via the upper end of the enclosure;
a lid, wherein the lid includes a plurality of openings, and wherein the plurality of openings expose the absorbent retaining portion to an exterior of the enclosure, wherein the lid is rotatably attached to the upper end of the enclosure via a hinge thereby allowing the lid to open and close over the upper end of the enclosure, wherein the hinge is disposed along the upper end of the enclosure, wherein when the lid is open, the ash retaining portion is uncovered, and wherein when the lid is closed, the ash retaining portion is covered by the lid;
a dispenser having a nozzle, wherein the dispenser is retained by the dispenser retaining portion, and wherein the dispenser stores and emits scented material; and
an absorbent, wherein the absorbent is retained by the absorbent retaining portion, and wherein the lid is configured to rotate about the hinge thereby entirely covering the ash retaining portion and simultaneously activating the nozzle of the dispenser to release the scented material into the absorbant.

2. The apparatus of claim 1, wherein the dispenser retaining portion includes a mechanical retention mechanism, wherein the dispenser retaining portion includes a guide, wherein the guide is configured such that the dispenser retaining portion is able to receive a specific type of dispenser,
and wherein the absorbent is removable from the absorbent retaining portion.

3. The apparatus of claim 2, wherein when the lid is closed, the lid presses down on the dispenser causing the dispenser to dispense the scented material into the absorbent.

4. The apparatus of claim 2, wherein the scented material stored within the dispenser is a scented spray.

5. The apparatus of claim 1, wherein the ash retaining portion extends from the upper end of the enclosure to the lower end of the enclosure.

6. The apparatus of claim 1, wherein the lid is press activated thereby causing the lid to rotate open, and wherein closing the lid causes the lid to activate a latch that maintains the lid closed.

7. The apparatus of claim 1, wherein the enclosure has a height and a diameter, wherein the diameter is at least two inches, and wherein the height is at least one and a half times the diameter.

8. The method of claim 1, wherein the enclosure has a height and a diameter, wherein the diameter is at least two inches, and wherein the height is at least one and a half times the diameter.

9. The apparatus of claim 1, wherein the ash retaining portion is a removable container that fits within the enclosure.

10. The apparatus of claim 1, wherein the upper end includes a plurality of ridges and at least one groove, wherein the plurality of ridges and the at least one groove each provide a support surface or brushing surface.

11. A method comprising:
forming an enclosure that has an ash retaining portion, an absorbent retaining portion, and a dispenser retaining portion, wherein the enclosure has an upper end and a lower end, and wherein the ash retaining portion is accessible via the upper end of the enclosure;
attaching a lid to the upper end of the enclosure via a hinge such that the lid opens and closes over the upper end of the enclosure, wherein the lid includes a plurality of openings, and wherein the plurality of openings expose the absorbent retaining portion to an exterior of the enclosure, wherein the hinge is disposed along the upper end of the enclosure, wherein when the lid is open, the ash retaining portion is uncovered, and wherein when the lid is closed, the ash retaining portion is covered by the lid;
attaching a dispenser to the dispenser retaining portion, wherein the dispenser stores and emits scented spray; and
attaching an absorbent to the absorbent retaining portion, wherein the lid is configured to rotate about the hinge thereby covering the ash retaining portion and dispensing the scented spray into the absorbent.

12. The method of claim 11, wherein the ash retaining portion extends from the upper end of the enclosure to the lower end of the enclosure.

13. The method of claim 11, wherein the lid is press activated such that pressing the lid down causes the lid to rotate open, and wherein closing the lid causes the lid to activate a latch that maintains the lid closed.

14. An apparatus comprising:
an enclosure having an attached lid that opens and closes, wherein the lid includes a plurality of openings, and wherein the plurality of openings expose an absorbent portion to an exterior of the enclosure, wherein the enclosure stores an ash retaining portion and a dispenser with a nozzle, wherein the ash retaining portion is accessible via the upper end of the enclosure, wherein the lid is attached to the upper end of the enclosure via a hinge, wherein the hinge is disposed along the upper end of the enclosure, wherein opening the lid exposes the ash retaining portion to outside the apparatus, wherein closing the lid covers the ash retaining portion, and wherein the dispenser stores scented material; and means for absorbing the scented material output by the dispenser when the lid is rotated about the hinge thereby covering the ash retaining portion and simultaneously triggering the nozzle of the dispenser to dispense the scented material into the means.

15. The apparatus of claim 14, wherein the means is an absorbent material, and wherein the apparatus is a portable scent dispensing ashtray.

16. The apparatus of claim 14, wherein the lid is press activated thereby causing the lid to rotate open, and wherein closing the lid causes the lid to activate a latch that maintains the lid closed.

17. The apparatus of claim 14, wherein the enclosure has a height and a diameter, wherein the diameter is at least two inches, and wherein the height is at least one and a half times the diameter.

\* \* \* \* \*